United States Patent [19]

van de Werken

[11] Patent Number: Plant 7,583

[45] Date of Patent: Jul. 9, 1991

[54] FORSYTHIA PLANT NAMED 'PYGMY-RED'

[75] Inventor: Hendrik van de Werken, Knoxville, Tenn.

[73] Assignee: The University of Tennessee Research Corporation, Knoxville, Tenn.

[21] Appl. No.: 271,666

[22] Filed: Nov. 16, 1988

[51] Int. Cl.[5] ..... A01H 5/00

[52] U.S. Cl. ..... Plt./54

[58] Field of Search ..... Plt./54

[56] References Cited

PUBLICATIONS van de Werken (1988) "Mutant Offspring", *American Nurseryman,* vol. 167, No. 1, Jan. 1, 1988, pp. 127–132.

Fincham, J. R. S. (1983), "Ionizing Radiation", *Genetics,* Jones and Bartlett Publishers, Inc., Boston, pp. 326–333.

Decourtye, L. (1978), "Utilisation de la mutagense pour l'obtention de nouvelles variét/ s d'Arbustes Ornementaux", Comptes Rendus des Seances D'Academie d'Agriculture de France, vol. 64(8), pp. 664–669.

"Arnoldia," vol. 31, No. 2, The Arnold Arboretum, Mar. 1971, pp. 41–63.

"Flowering Shrubs," Zucker, Isabel, 1966, D. Van Nostrand Co., Inc., New York, NY, p. 380.

"Hilliers Manual of Trees & Shrubs," 2nd American Edition, Hilliers & Sons Ltd., 1979, A. S. Barnes & Co., Cranbury, NJ, p. 575.

"Hortus Third, A Concise Dictionary of Plants Cultivated in the United States and Canada," Staff of L. H. Bailey Hortorium, Cornell University, 1976, MacMillan Publishing Co., New York, NY, p. 1290.

"Manual of Woody Landscape Plants—Their Identification, Ornamental Characteristics, Propagation and Uses," Dirr, Michael A., 1983, Stipes Publishing Co., Champaign, IL, p. 826.

*Primary Examiner*—James R. Feyrer

*Attorney, Agent, or Firm*—William H. Elliott, Jr.

[57] ABSTRACT

A new cultivar of Forsythia named 'Pygmy-Red' characterized by its small shrub size, its narrow foliage, and the distinct red color of its currently matured shoots.

3 Drawing Sheets

This invention relates to a new cultivar of Forsythia named "Pygmy-Red", which is characterized especially by its low growth habit, its narrow leaves, and the red color of current shoots at maturity.

The new variety was derived as a seedling from a vegetative line of mutants, which had been produced in turn by subjecting rooted cuttings of parent "Lynwood Gold" (a sport of *F. intermedia* "Spectabilis").

In 1968, three hundred cuttings of "Lynwood Gold" that had been potted and held in cold storage (38° F.) for six weeks and then returned to the greenhouse for two days were irradiated with 1200 rad fast neutrons. One of the plants of this group that broke dormancy formed a shoot with variegated foliage. This plant was cut back repeatedly to induce branching and eventually formed shoots that exhibited different characteristics. Each shoot was propagated by stem cuttings over 10 vegetative generations of selection and propagation. From this plant population two vegetatively selected types and three seedlings were selected. Further propagation and testing of these selections over several more years were shown to be the stable and new forsythia varieties that are the subject of this and four other copending plant patent applications; viz:

| Ser. No. | Name | Type |
|---|---|---|
| 272,063 | "Lemon-Screen" | vegetative selection |
| 273,489 | "Tinkle Bells" | vegetative selection |
| 271,919 | "Minikin" | seedling |
| 271,665 | "Fairy Land" | seedling |
| 271,666 | "Pygmy-Red" | seedling |

Each differs greatly from the parent "Lynwood Gold" and also from one another.

"Pygmy-Red" was selected at the seedling stage because of its distinct foliage form and growth characteristics. The seedling showed good growth characteristics in the field, a distinct red coloration in mature current year shoots, and maroon fall color on the upper side of the leaves. Cuttings from this plant have been rooted in soil and asexually propagated, and its progeny have displayed homogeneous and stable characteristics.

Throughout this specification, color names beginning with a small letter signify that the name of the color as used in common speech are aptly descriptive. Color names beginning with a capital letter designate values based on the R.H.S. Colour Chart, published by The Royal Horticultural Society of London, England.

The accompanying drawings illustrate the new variety in color as grown in Knox County within the State of Tennessee.

Figure 1:
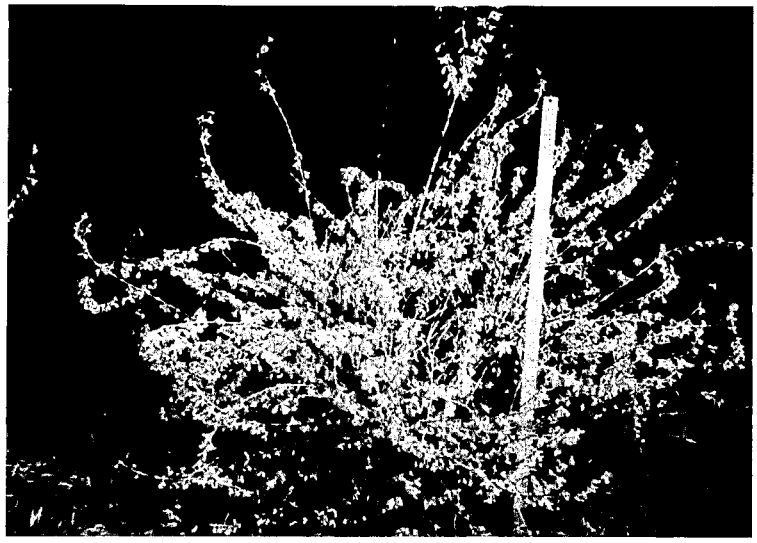
FIG. 1 illustrates "Pygmy-Red" in spring bloom. The measuring stick is set on the ground and is 4 ft. long.
Figure 2:
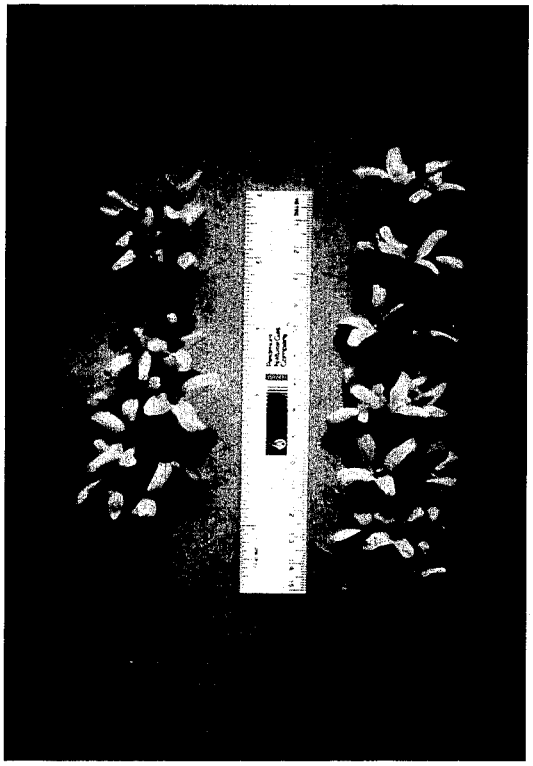
FIG. 2 shows lowered cut stems.
Figure 3:
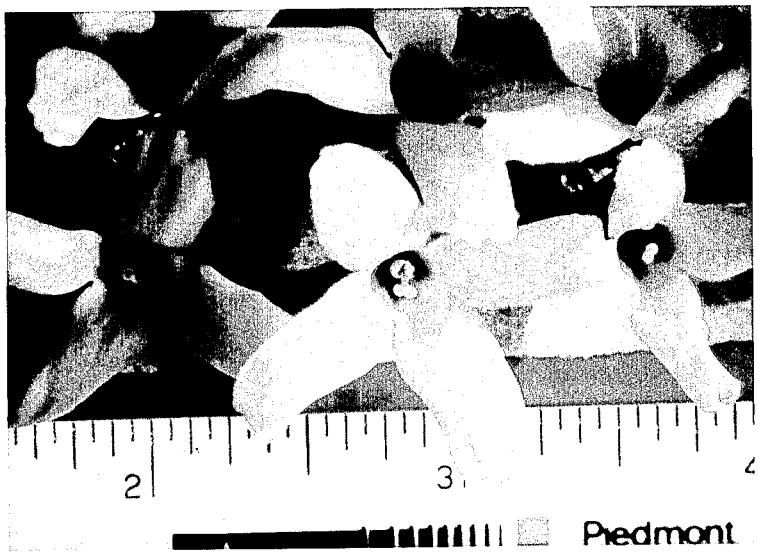
FIG. 3 is a close-up view of the flowers of FIG. 2 which also illustrates the red color of the currently matured shoots.
Figure 4:
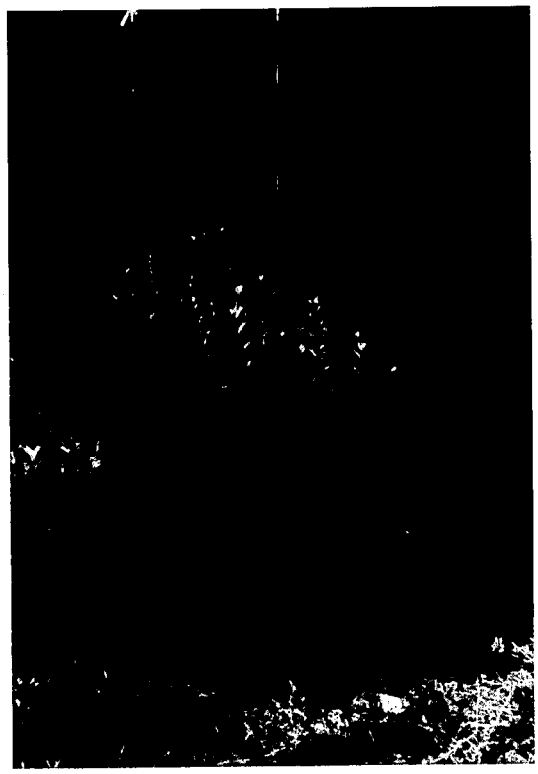
FIG. 4 illustrates the "Pygmy-Red" plant in May foliage.
Figure 5:
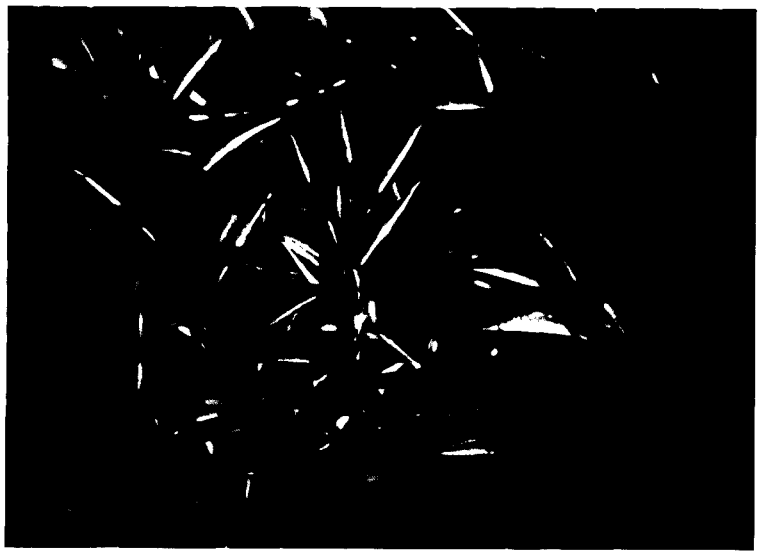
FIG. 5 is a closer view of the foliage shown in FIG. 4.

The following characteristics distinguish "Pygmy-Red" from its parent and other Forsythia cultivars:

THE PLANT

"Pygmy-Red" has a low growth habit. The plant form is loose, but graceful, some branches bending to the ground and rooting where they touch the soil. The plant is a hardy (to Zone 6b or lower), shows good vigor but develops few seed pods. It is a flowering shrub, blooming readily when used for forcing into flower in a greenhouse and suitable for containers. The ultimate size of "Pygmy-Red" is about 3½ to 4½ ft. in height and 5 ft. to 6 ft. wide. The size of "Pygmy-Red" makes it particularly useful for road median planting, small visual and physical landscape screens and barriers, or for mass planting in parks. The plant requires minimal pruning and has disease and insect-resistant foliage.

Its parent, "Lynwood Gold", by contrast is tall and slender—a straight upright variety with erect stems and which attains a height of 6 ft. to 7½ ft. at maturity.

FLOWER

"Pygmy-Red" flowers at an intermediate stage. The yellow flowers (Yellow 6A in color) are 1¼ in. to 1½ in. diameter and generally have four, but sometimes five, petals. The corolla lobes are narrow. The pistils extend 2/25 in. to 3/25 in. above the pollen sacs of the stamen. The plant produces two flowers per node on the flowering wood, which has internodes ½ in. to 1½ in. in length.

SHOOTS

The currently matured Pygmy-Red shoots have a distinct red color (Purple Red 59 A); high anthocyanin pigmentation of the mature current shoots is also expressed in the maroon fall color of the foliage when the plant is grown with full exposure to direct sunlight. The shoots are lamellate between nodes, flexible, bending to touch the ground, which leads to self-propagation by layering.

The stems of the "Lynwood Gold" parent are green when young and brown when mature; they are a bit stiff; the pith at the nodes is lamellate, and on one year shoots, the stems between nodes are hollow.

FOLIAGE

The "Pygmy-Red" leaves are dark green in color when both young and mature. The leaves are simple, serrate and lanceolate, being acuminate at the tip and attenuate at the base, 0.3 in. to 0.4 in. wide and 2 in. to 2½ in. long on flowering wood. The leaves on vegetative shoots are somewhat larger, up to 1 in. wide and 2¾ in. long. Venation is pinnate. Few, if any, lobed leaves occur on vegetative shoots, as often occurs with other Forsythia cultivars. Even on fast growing vegetative shoots, the internodes are less than 1½ in. long.

The leaves of the "Lynwood Gold" parent, on the other hand, are ovate lanceolate in shape and about 3" to 4½" long and about 1" to 1½" wide. Both young and old leaves are deep green in color.

To facilitate the comparison of the characteristics and features of "Pygmy-Red", the subject of this application, and its parent, "Lynwood Gold" and also with the four other new mutant offspring varieties of "Lynwood Gold" referred to above, there are attached hereto as Tables 1–5 comparative tabulations of the characteristics and properties of parent and its five offspring mutants that were developed from a single irradiated plant of "Lynwood Gold." Table 1 compares "Pygmy-Red" and its parent "Lynwood Gold". Table 2 compares "Pygmy-Red" and "Fairy-Land". Table 3 compares "Pygmy-Red" and "Tinkle Bells". Table 4 compares "Pygmy-Red" and "Minikin". Table 5 compares "Pygmy-Red" and "Lemon Screen".

TABLE 1

| | S/N: 271,666 PYGMY RED | LYNWOOD GOLD |
|---|---|---|
| Plant: | | |

TABLE 1-continued

| | S/N: 271,666 PYGMY RED | LYNWOOD GOLD |
|---|---|---|
| Habit | Low, loose graceful arching to ground | Tall, slender-Upright straight & erect stems |
| Size, height | 3½'–4½' | 6'–7½' |
| Size, width | 5'–6' | |
| Vigor | Good vigor | |
| Hardiness | Hardy Zone 6b (or lower) | |
| Productivity | Readily roots where branches touch ground few seed pods | Fertile |
| Stems: | | |
| Color (young) | High anthocyanin | Green |
| Color (mature) | Purple Red (59 A) | Brown |
| Rigidity | Flexible lamellate between nodes | A bit stiff; pith nodes lamellate; hollow between nodes on one year shoots |
| Leaves: | | |
| Type | Simple | |
| Color: | | |
| (young) | Dark Green | Deep Green |
| (mature) | Dark Green | Deep Green |
| (fall) | Anthocyanin (maroon) expressed in full sun | |
| Shape | Lanceolate (few lobed leaves on vegetative shoots) | ovate lanceolate |
| tip | Accuminate | |
| base | Attenuate | |
| margins | Serrate | |
| Size: | | |
| length | 2"–2½" on flowering wood; to 2¾" on vegatative wood | 3–4½" |
| width | 0.3"–0.4" on flowering wood; to 1" on vegetative wood | 1–1½" |
| Venation | Pinnate | |
| Flower: | | |
| Date of Flowering | Intermediate | Late |
| Size: width | 1¼"–1½" | 1"–1½" (medium) |
| Color: | Yellow (7A) | Brillant Yellow (lighter than its parent Spectabilis) |
| Corolla: | | |
| length | | |
| lobes | Narrow | Reflexed |
| Petals: number | 4 - sometimes 5 | Large, broad, open Elliptic |
| Pistils: | Extend 2/25"–3/25" above pollen sacs of stamens | Extend well above pollen sacs (anthers) of stamens |
| Number per node: | 2 | |
| Insertion angle on upright stems: | | |
| Internodes: | 1"–1½" (1½" even on fast growing shoots) | Flowers almost evenly spaced on stems |
| Stress Resistance: | disease and insect | |
| Utility Aspects: | | |

TABLE 2

| | S/N: 271,666 PYGMY RED | S/N 271,665 FAIRY LAND |
|---|---|---|
| Plant: | | |
| Habit | Low, loose graceful arching to ground | Small overall & fine textured: Closely spaced flowers & leaves Dense (young) foliage |
| Size, height | 3½'–4½' | 3'–4' |
| Size, width | 5'–6' | 5'–6' |
| Vigor | Good vigor | Good vigor for size |
| Hardiness | Hardy Zone 6b | Zone 6b (or lower) |

TABLE 2-continued

| | S/N: 271,666 PYGMY RED | S/N 271,665 FAIRY LAND |
|---|---|---|
| | (or lower) | |
| Productivity | Readily roots where branches touch ground few seed pods | Few seed pods |
| Stems: | | |
| Color (young) | High anthocyanin | Light green |
| Color (mature) | Purple Red (59 A) | Brownish green |
| Rigidity | Flexible lamellate between nodes | Very flexible lamellate between nodes |
| Leaves: | | |
| Type | Simple | Simple |
| Color: | | |
| (young) | Dark Green | Medium green (fairly light) |
| (mature) | Dark Green | Medium green (fairly light) |
| (fall) | Anthocyanin (maroon) expressed in full sun | Mostly faded yellow |
| Shape | Lanceolate (few lobed leaves on vegetative shoots) | Lanceolate |
| tip | Accuminate | Accuminate |
| base | Attenuate | Attenuate |
| margins | Serrate | On flowering wood; entire On vegetative wood: serrate top ⅓ |
| Size: | | |
| length | 2"–2½" on flowering wood; to 2¾" on vegatative wood | On flowering wood: 1½"–2½" On vegatative shoots: about 3" |
| width | 0.3"–0.4" on flowering wood; to 1" on vegetative wood | On flowering wood: 0.2"–0.4" On vegatative shoots 0.5–0.6" |
| Venation | Pinnate | Pinnate |
| Flower: | | |
| Date of Flowering | Intermediate | Intermediate |
| Size: width | 1¼"–1½" | ¾"–1¼" |
| Color: | Yellow (7A) | Yellow (6 A) |
| Corolla: | | |
| length | | |
| lobes | Narrow | Reflexed, small |
| Petals: number | 4 - sometimes 5 | Generally 4-many have 5, 6, 7 and 8 on single corolla |
| Pistils: | Extend 2/25"–3/25" above pollen sacs of stamens | Extend 3/25" to 4/25" above pollen sacs (anthers) of the stamen |
| Number per node: | 2 | 2–4 |
| Insertion angle on upright stems: | | |
| Internodes: | 1"–1½" (1½" even on fast growing shoots) | ¼" to about 1" |
| Stress Resistance: | disease and insect | |
| Utility Aspects: | | Very well suited for container culture |

TABLE 3

| | S/N: 271,666 PYGMY RED | S/N 273,489 TINKLE BELLS |
|---|---|---|
| Plant: | | |
| Habit | Low, loose graceful arching to ground | Semi-dwarf; Upright |
| Size, height | 3½'–4½' | 4'–4½' |
| Size, width | 5'–6' | |
| Vigor | Good vigor | Medium vigor |
| Hardiness | Hardy Zone 6b (or lower) | Hardy Zone 6b (or lower) |
| Productivity | Readily roots where branches touch ground few seed pods | Does not layer naturally (replicates from stools (no seed pods observed) |
| Stems: | | |
| Color (young) | High anthocyanin | Yellow Green |
| Color (mature) | Purple Red (59 A) | Light brown |
| Rigidity | Flexible lamellate between nodes | Sparsely lamellate between nodes - Rigid |
| Leaves: | | |
| Type | Simple | Simple |
| Color: | | |
| (young) | Dark Green | Medium green |
| (mature) | Dark Green | Medium green |
| (fall) | Anthocyanin (maroon) expressed in full sun | Faded green to yellow |
| Shape | Lanceolate (few lobed leaves on vegetative shoots) | Elliptical |
| tip | Accuminate | Acute on flower shoots accuminate on vegetative shoots |
| base | Attenuate | |
| margins | Serrate | serrate on upper ⅓ near tip |
| Size: | | |
| length | 2"–2½" on flowering wood; to 2¾" on vegatative wood | 2"–3" (with petiole) |
| width | 0.3"–0.4" on flowering wood; to 1" on vegetative wood | ½" |
| Venation | Pinnate | Pinnate |
| Flower: | | |
| Date of Flowering | Intermediate | Early |
| Size: width | 1¼"–1½" | ½"–¾" at 45° angle |
| Color: | Yellow (7A) | Bright Yellow (7 B) |
| Corolla: | | |
| length | | ½" open to 45° angle |
| lobes | Narrow | not reflexed during prime |
| Petals: number | 4 - sometimes 5 | 4; occasionally 5 or 6 |
| Pistils: | Extend 2/25"–3/25" above pollen sacs of stamens | short: anthers slightly below stigma portion of pistil |
| Number per node: | 2 | 2; often 4 per node |
| Insertion angle on upright stems: | | buds & flowers pendulous |
| Internodes: | 1"–1½" (1½" even on fast growing shoots) | ½"–1½" |
| Stress Resistance: | disease and insect | Disease and insect |
| Utility Aspects: | | Can force flowering suitable for container culture |

TABLE 4

| | S/N: 271,666 PYGMY RED | S/N 271,919 MINIKIN |
|---|---|---|
| Plant: | | |
| Habit | Low, loose graceful arching to ground | Small stature, fine textured; small leaves and small stems; densely foliated |
| Size, height | 3½'–4½' | 2'–2½' |
| Size, width | 5'–6' | 3'–4' |
| Vigor | Good vigor | Good vigor but slow growth |
| Hardiness | Hardy Zone 6b (or lower) | Zone 6b (or lower) |
| Productivity | Readily roots where branches touch ground few seed pods | Layers naturally Abundant seed pods |
| Stems: | | |
| Color (young) | High anthocyanin | Light green |
| Color (mature) | Purple Red (59 A) | Brownish green |
| Rigidity | Flexible lamellate between nodes | Ascending strongly lamellate between |

TABLE 4-continued

| | S/N: 271,666 PYGMY RED | S/N 271,919 MINIKIN |
|---|---|---|
| | | nodes |
| Leaves: | | |
| Type | Simple | Simple |
| Color: | | |
| (young) | Dark Green | Bright green to dark green |
| (mature) | Dark Green | Bright green to dark green |
| (fall) | Anthocyanin (maroon) expressed in full sun | Fading green until leaf drop |
| Shape | Lanceolate (few lobed leaves on vegetative shoots) | Linear |
| tip | Accuminate | Accuminate |
| base | Attenuate | Attenuate |
| margins | Serrate | Lightly serrate |
| Size: | | |
| length | 2"–2½" on flowering wood; to 2¾" on vegatative wood | On vegetative shoots- 1½" attached to ¼" long slender petiole; smaller on flowering shoots |
| width | 0.3"–0.4" on flowering wood; to 1" on vegetative wood | On vegetative shoots - ¼"; |
| Venation | Pinnate | Pinnate |
| Flower: | | |
| Date of Flowering | Intermediate | Intermediate |
| Size: width | 1¼"–1½" | ½"–¾" (cup shaped) fully reflexed |
| Color: | Yellow (7A) | Yellow (9 A) |
| Corolla: | | |
| length | | |
| lobes | Narrow | strongly reflexed, very small |
| Petals: number | 4 - sometimes 5 | 4:- short and recurved |
| Pistils: | Extend 2/25"–3/25" above pollen sacs of stamens | Short; 1/25" below pollen sacs of stamens |
| Number per node: | 2 | 2–4 |
| Insertion angle on upright stems: | | |
| Internodes: | 1"–1½" (1½" even on fast growing shoots) | Short (Flowering shoots ¼–¾" Vegetative shoots up to 2") |
| Stress Resistance: | disease and insect | Doesn't require same degree of winter protection as most container grown plants of genre |
| Utility Aspects: | | Blooming can be forced. Expecially suited for container culture. |

TABLE 5

| | S/N: 271,666 PYGMY RED | S/N 272,063 LEMON SCREEN |
|---|---|---|
| Plant: | | |
| Habit | Low, loose graceful arching to ground | Tall, open and graceful; Upright, fan shape; vigorous; open |

TABLE 5-continued

| | S/N: 271,666 PYGMY RED | S/N 272,063 LEMON SCREEN |
|---|---|---|
| | | foliage |
| Size, height | 3½'–4½' | Up to 10' |
| Size, width | 5'–6' | Hardy Zone 6b (or lower) |
| Vigor | Good vigor | Vigorous |
| Hardiness | Hardy Zone 6b (or lower) | |
| Productivity | Readily roots where branches touch ground few seed pods | Abundant Flowers/ highly sterile/pruned wood branches quickly |
| Stems: | | |
| Color (young) | High anthocyanin | |
| Color (mature) | Purple Red (59 A) | Yellow |
| Rigidity | Flexible lamellate between nodes | Slightly lamellate between nodes |
| Leaves: | | |
| Type | Simple | Simple |
| Color: | | |
| (young) | Dark Green | Yellow green 151 B or Chartreuse (appear after flowering) |
| (mature) | Dark Green | Normal green (Yellow-Green 144) whitish blotches |
| (fall) | Anthocyanin (maroon) expressed in full sun | Greyed Purple 187 B |
| Shape | Lanceolate (few lobed leaves on vegetative shoots) | |
| tip | Accuminate | Accuminate |
| base | Attenuate | Attenuate |
| margins | Serrate | Serrate |
| Size: | | |
| length | 2"–2½" on flowering wood; to 2¾" on vegatative wood | Not distinguishing |
| width | 0.3"–0.4" on flowering wood; to 1" on vegetative wood | Not distinguishing |
| Venation | Pinnate | Pinnate |
| Flower: | | |
| Date of Flowering | Intermediate | Early |
| Size: width | 1¼"–1½" | 1½"–1¾" |
| Color: | Yellow (7A) | Yellow (6 C) |
| Corolla: | | |
| length | | |
| lobes | Narrow | Somewhat reflexed |
| Petals: number | 4 - sometimes 5 | 4, sometimes fasciated |
| Pistils: | Extend 2/25"–3/25" above pollen sacs of stamens | aborted stamens &/or pistils |
| Number per node: | 2 | 4 to 8 |
| Insertion angle on upright stems: | | |
| Internodes: | 1"–1½" (1½" even on fast growing shoots) | 1" to 2" long on flowering wood |
| Stress Resistance: | disease and insect | Summer foliage disease & insect resistant |
| Utility Aspects: | | Summer pruning leads to shoot with chartreuse leaves (young) |

What is claimed is:

1. A new and distinct cultivar of Forsythia named 'Pygmy-Red', substantially as shown and described herein.

* * * * *